(12) United States Patent
Kronestedt et al.

(10) Patent No.: US 8,617,109 B2
(45) Date of Patent: Dec. 31, 2013

(54) DEVICE FOR DELIVERING MEDICAMENT

(75) Inventors: Victor Kronestedt, Stockholm (SE); Lennart Brunnberg, Tyresö (SE); Stephan Olson, Stockholm (SE); Tomas Deurell, Årsta (SE); Anders Karlsson, Saltsjö-boo (SE)

(73) Assignee: SHL Group AB, Nacka Strand (SE)

(*) Notice: Subject to any disclaimer, the term of this patent is extended or adjusted under 35 U.S.C. 154(b) by 1234 days.

(21) Appl. No.: 11/916,082

(22) PCT Filed: May 22, 2006

(86) PCT No.: PCT/SE2006/050150
§ 371 (c)(1),
(2), (4) Date: Aug. 22, 2008

(87) PCT Pub. No.: WO2006/130100
PCT Pub. Date: Dec. 7, 2006

(65) Prior Publication Data
US 2010/0186739 A1    Jul. 29, 2010

Related U.S. Application Data

(63) Continuation-in-part of application No. 11/140,989, filed on Jun. 1, 2005, now abandoned, and a continuation-in-part of application No. 11/282,593, filed on Nov. 21, 2005.

(30) Foreign Application Priority Data
Jun. 1, 2005   (EP) ..................................... 05104734

(51) Int. Cl.
*A61M 5/20*       (2006.01)
*A61M 5/00*       (2006.01)
*A61M 5/315*      (2006.01)
*A61M 11/00*      (2006.01)

(52) U.S. Cl.
USPC ....... 604/135; 604/211; 604/224; 128/200.14

(58) Field of Classification Search
USPC ............. 604/68, 71, 134–137, 192, 197, 198, 604/207–211, 223, 224; 128/200.14
See application file for complete search history.

(56) References Cited

U.S. PATENT DOCUMENTS

| 5,104,380 A | 4/1992 | Holman et al. |
| 5,320,609 A | 6/1994 | Haber et al. |

(Continued)

FOREIGN PATENT DOCUMENTS

| EP | 0338806 A2 | 10/1989 |
| GB | 2 109 690 A | 6/1983 |

(Continued)

OTHER PUBLICATIONS

PCT International Search Report, mailed Sep. 15, 2006, in connection with International Application No. PCT/SE2006/050150.

*Primary Examiner* — Nicholas Lucchesi
*Assistant Examiner* — Nathan R Price
(74) *Attorney, Agent, or Firm* — Potomac Patent Group PLLC

(57) ABSTRACT

The present invention relates to a device for the delivery of predetermined doses of liquid medicament to a patient, which medicament is intended to be inhaled by the patient or intended to be injected into the body of the patient. The device is adapted to be in a medicament delivery state and in a medicament non-delivery state. When the device is in a medicament delivery state, said device is adapted to drive a piston into a cartridge containing the liquid medicament to be delivered, with a force that is above or equal to a predetermined minimum force value and below a predetermined maximum force value. The minimum force value is the lowest force value needed to deliver the predetermined dose and the maximum force value is the first force value at which it exists a risk of damaging the cartridge or the components of the device. Further, more of the spring force is brought to an efficient output torque ensuring that a predetermined volume of medicament is expelled from a cartridge.

11 Claims, 11 Drawing Sheets

(56) References Cited

U.S. PATENT DOCUMENTS

| | | |
|---|---|---|
| 5,478,316 A | 12/1995 | Bitdinger et al. |
| 5,626,566 A | 5/1997 | Petersen et al. |
| 2002/0120235 A1* | 8/2002 | Enggaard .................. 604/135 |

FOREIGN PATENT DOCUMENTS

| | | |
|---|---|---|
| WO | 0187384 A1 | 11/2001 |
| WO | 02053214 A1 | 7/2002 |

* cited by examiner

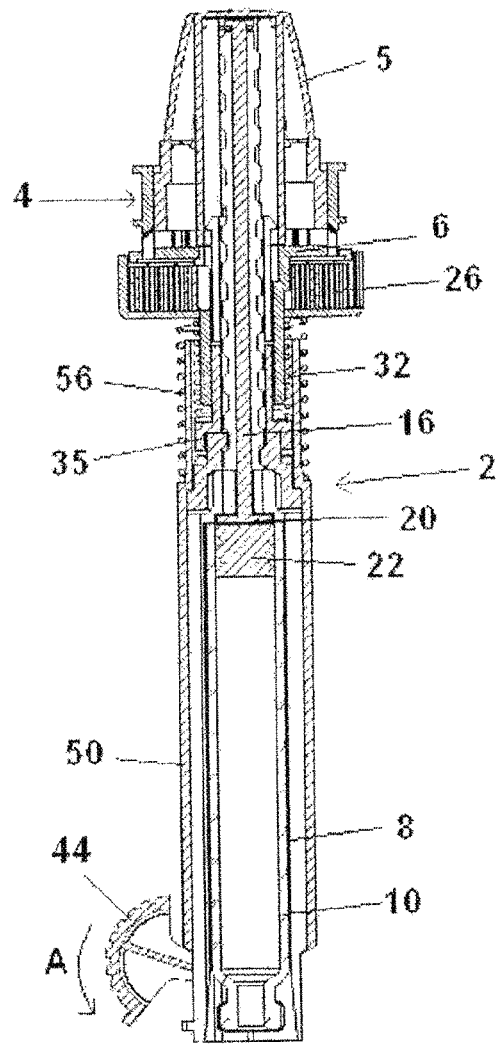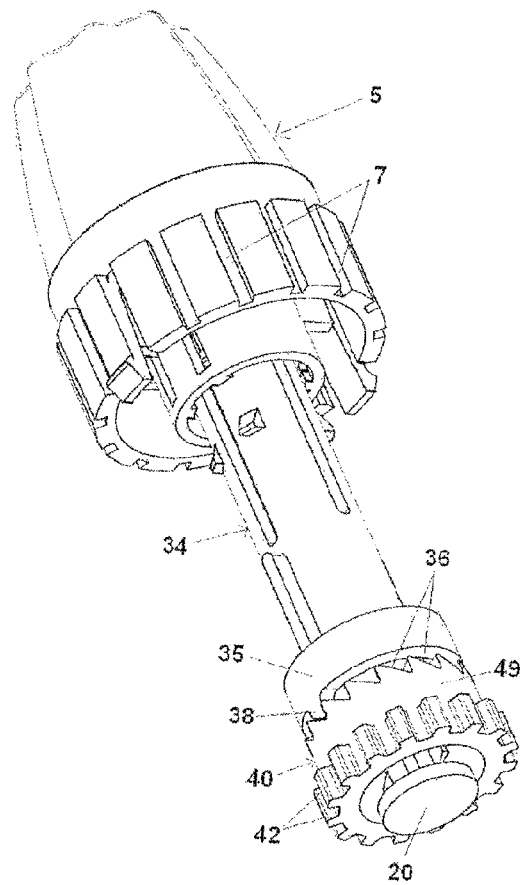
Figure 1
Figure 2

DEVICE FOR DELIVERING MEDICAMENT

TECHNICAL FIELD

The present invention relates to a device for the delivery of predetermined doses of liquid medicament to a patient, which medicament is intended to be inhaled by the patient or intended to be injected into the body of the patient. The device is adapted to be in a medicament delivery state and in a medicament non-delivery state. When the device is in a medicament delivery state, said device is adapted to drive a piston into a cartridge containing the liquid medicament to be delivered, with a predetermined force value. Said force is preferably above or equal to a predetermined minimum force value and below a predetermined maximum force value.

BACKGROUND ART

The development of devices for delivering liquid medicament to a patient, have during the recent years become more and more directed towards the ability for the patient themselves to administer the medicament with a predetermined dose in an easy, safe and reliable way and also to facilitate the administration of medicaments for hospital personnel in the same facilitated way. Depending on the intended use and type of medicament, they have developed a varying degree of automatic functions.

Currently existing automatic medicament delivery devices, conventionally comprise a cartridge or the like, containing the liquid medicament to be delivered. Said conventional delivery device is further provided with a plunger rod that is adapted to be in contact with a piston provided inside the cartridge. Upon delivery of the medicament contained in the cartridge, the plunger rod will exert a force upon the piston, whereupon the piston will move forward inside the cartridge and thus expel the medicament from the cartridge. The distance that the piston moves inside the cartridge, determines the amount of medicament to be delivered.

The force that is applied to the piston during medicament delivery is generally accomplished by means of having a pre-tensed helical spring connected to the plunger rod and thus provided in the interior of the delivery device, wherein the force is obtained in accordance with Hooke's law (1):

$$F = -k*y \qquad (1)$$

wherein F is the force exerted by the spring (N), y is the displacement of the spring from its original position (m) and k is the spring constant (N/m).

From Hookes law follows that the force acting on the piston will decline linearly as the piston moves forward in the cartridge. Thus, when a large volume of medicament is to be expelled from the cartridge, the force needs to be initially high in order to be able to move the piston all the way down to the required position of the piston in the cartridge. However, the conventional cartridge is often made of an easily breakable material, such as glass, and having an initial high force acting on the piston will result in that there is a substantial risk of damaging the cartridge, which is most undesirable.

Having for instance a high viscosity medicament contained in the cartridge or having a fine needle attached to the delivery device will also require a higher force to act on the piston. The same applies for situations when the medicament is to be delivered within a short period of time. One can generally say that when a plunger rod is allowed to freely act on the piston, there is a substantial risk of damaging the cartridge when the piston is applied with a force that is above or equal to approximately 50-60 N.

One solution to the problem is to provide the delivery device with a spring having a smaller spring constant, i.e. the gradient in the force-way diagram will have more flat appearance and the initial force acting on the piston will be decreased. However, a smaller spring constant would require a larger spring and hence a larger device. A larger device is generally not handled as easily as a device with a smaller size. Another problem is, that there is a minimum force value required to initially act on the piston in order for the piston to start the movement from its original position in the distal end of the cartridge, which minimum force in the art often is referred to as the "break loose force". This force would not be obtained if the device was provided with a spring having a too small spring constant.

Also, the force acting on the piston is higher during the beginning of the medicament delivery procedure than towards the end, which results in that the piston moves faster in the beginning than in the end of said procedure, i.e. the medicament is during the procedure delivered to the patient at a higher rate in the beginning than in the end. This is undesirable, especially when the medicament is to be inhaled by the patient. This phenomena also results in that the rate with which the medicament is delivered may differ from one dose to another, since a higher dose requires an initially higher force to act on the piston than a lower dose, i.e. the so called "dose-to-dose accuracy" is poor with prior art automatic delivery devices.

Moreover, the conventional cartridge does not always have a smooth interior surface but may exhibit irregularities or unevenness as a result from the manufacturing procedure or as a result from the lubrication procedure, since the interior of the conventional cartridge most often is lubricated before use, for instance by the use of silicon oil. Such an irregularity or unevenness may increase the travel resistance acting on the piston which may cause the piston to slow down or even get stuck before it has reached its predetermined position inside the cartridge, especially if the irregularity is to be found towards the end of the distance that the piston is required to travel when the force acting on it has declined to a low value. It is generally known in the art that the force acting on the piston should not be below approximately 5 N, which thus is the lowest sliding force value needed in order not to allow the piston to get stuck before the entire set dose has been delivered.

Another problem is that the conventional delivery devices are generally made of plastic material due to manufacturing and economical reasons. Having a pre-tensed spring provided in the interior of such a device, results in that the tension caused by the pre-tensed spring, is held back by means of plastic components, which can lead to creep and hence plastic deformation of the plastic materials. This may reduce the life of the device and affect its accuracy and may also affect the automatic delivery function of said device. Also, having a high force acting on the piston during medicament delivery can cause damage of the plastic components of the device, which thus is another reason why it is not suitable to have a too high force applied to the piston, besides the risk of damaging the cartridge.

It is also important that the user of the delivery device is able to set the amount of medicament that is to be delivered in a relatively easy and reliable way. Likewise it is important and highly desired that such a delivery device is able to target specific time limits, for instance a predetermined injection time or deliver a dose within a determined time range.

GB 2109690 describes a dose metering device that uses a mechanism operated by rotation of a cap mounted concentrically around a pen barrel. This rotational movement of the externally mounted cap is converted via a rotary ratchet and pawl mechanism and via a lead screw mechanism into axial movement of a rotating screw which drives a plunger down a cartridge in the barrel and expresses the dose. For some users the actual step of manually expressing the dose causes anxiety and devices which automatically can express a dose on demand would be attractive.

According to the patent document U.S. Pat. No. 5,104,380 this has been achieved by a syringe device comprising a body and a rotatable dose setting device mounted on the body and capable of being moved to a selected set position, a latch arranged to retain the setting device in the set position, and means arranged to release the latch to cause the set dose to be expelled. Movement of the dose setting device to the selected set position is accompanied by rotational straining of a spiral spring, which, when the latch is released, provides the force for expelling the set dose. When the latch is released, the setting device is returned to an original position to drive a plunger through a one-way clutch to expel the set dose. The disclosed driving means comprises a quick pitch screw thread arrangement for transforming rotation of the setting device into linear movement of the plunger. The body is adapted for receiving a cartridge containing a fluid to be injected by having a cartridge container removable from the body for insertion of a cartridge and then removal of the cartridge container is arranged to release the quick pitch screw thread device thus allowing the plunger to be returned to an initial position. However, this pen syringe does not offer neither the opportunity to cancel a set dose, so if a dose once set is not wanted for injection the only way to bring the syringe back in its neutral position is to spill the dose. With syringes by which large doses may be set or in case the medicine is very expensive, as is the case with growth hormone, this is not acceptable.

In order to solve the problem with dose cancelling, the patent document U.S. Pat. No. 5,626,566 A discloses a pen shaped syringe for repetitive injection of individually, set doses of a medicine from a cylinder ampoule reservoir, comprising a dose setting member which allow a dose set to be cancelled by incorporating means provided to release a unidirectional coupling between a piston drive member and the dosing member. However, this design both requires a release mechanism to be actuated when a dose is to be reset as well as a manual actuating mechanism when the medicine is to be expressed.

In the above mentioned devices the characteristics of the springs are such that the spring force increases proportionally with the deformation so that the force is initially high in order to be able to move the piston to the required position of the piston in a cartridge and fading out during the movement.

U.S. Pat. No. 5,478,316 (Bitdinger et al) describes a device for automatic injection of a material into the body. In order to avoid the high impact of prior art devices, the device is provided with a constant force spring for moving a syringe assembly with respect to a housing and towards the skin of the patient, and for urging a rod in the direction of a piston provided inside a cartridge. The force exerted by the constant force spring is said to be sufficient to overcome the friction between the piston and the cartridge and between the needle and the user's skin.

Even though U.S. Pat. No. 5,478,316 describes the avoidance of a high impact, the device disclosed is not provided with means in order to set the force exerted on the rod to a predetermined force value, thus the advantage of applying a force to the rod that is within a predetermined force range is not described. Moreover, the device is not provided with means in order to set a predetermined dose of medicament to be delivered.

In order to solve the problem with both high impact and dose setting, WO 01/87384 A1 describes an injection device for injecting set doses from a container, which doses are set by operation of a dose setting button by which operation elastic torsion rods positioned parallel with the longitudinal axis of the device are twisted. By the dose setting a torque is transmitted from the dose setting button to the rods through gear transmissions comprising a toothing carried by a tubular part coupled to the dose setting button to rotate with this button. The toothing engages pinions fixed to the proximal ends of the torsion rods, which are made from a super elastic material, which can stand a deformation larger than 2% without being permanently deformed. However, this injection device does not offer the opportunity to cancel a dose or the opportunity to accumulate more energy in order to deliver a large dose or predetermined doses at multiple injection sites. Moreover, the device has the torsion rods positioned alongside of the cartridge, which is not favourable in the case when a torsion rod breaks, since said break can damage the cartridge.

It is also known that the finer the pitch of grooving, i.e. the finer the screw pitch in the interior of a drive nut, i.e. the finer the pitch of grooving of the thread on a rod, the higher the force provided to the piston. Further, none of the above mentioned documents mention how to bring more of a spring force to an efficient output torque.

SUMMARY OF THE INVENTION

The object of the present invention is therefore to provide an automatic liquid medicament delivery device, which during medicament delivery applies a force with a predetermined spring force value to a piston and brings more of the spring force to an efficient output torque ensuring that a predetermined volume of medicament is expelled from a cartridge.

The present invention also substantially lowers the risk of damaging the cartridge and/or the device during medicament delivery in comparison with prior art automatic liquid medicament delivery devices.

The inventive delivery device also substantially improves the dose and the dose-to-dose accuracy in comparison with prior art devices.

With the present invention it also possible to set the predetermined dose that is to be delivered in an easy and reliable way.

Another object of the present invention is to provide an automatic liquid medicament delivery device, which substantially reduces the problems with creep in and plastic deformation of the plastic materials of the delivery device.

With the inventive delivery device it is also possible to deliver the predetermined dose in multiple administration steps.

These objects are accomplished with a delivery device according to the preamble of the independent claim provided with the features according to the characterizing portions of the independent claim.

According to an aspect of the present invention, there is provided a device for delivery of predetermined doses of liquid medicament, which device is adapted to be in a medicament delivery state and in a medicament non-delivery state, said device is adapted to comprise;
   a cartridge adapted to contain the liquid medicament and a
      piston sealingly and slidably arranged in said cartridge;

an energy accumulating member adapted to accumulate energy in terms of at least one predetermined step when the device is in the medicament non-delivery state;

an elongated threaded plunger rod adapted to be arranged in the interior of the device;

a plunger rod driving member engaged to the threaded plunger rod and adapted to be in a driven state when the device is in the medicament delivery state and adapted to be in a non-driven state when the device is in the medicament non-delivery state, wherein the rotation of the plunger rod driving member due to the output torque of energy accumulating member drives the threaded plunger rod and allows said rod which is in contact with the piston, to be driven towards the proximal end of the cartridge with a predetermined distance and expels a predetermined dose of the liquid medicament from the cartridge; wherein a bearing coupled to or supported on an outer cover is arranged and designed to effectively pick up forces acting on the proximal part of the device in the longitudinal direction thereof; whereby more of the accumulated energy that results from the stepwise rotational tensioning of the energy accumulating member positioned at the distal end of the device, is brought to an efficient output torque.

According to another aspect of the present invention, the energy accumulating member is a flat spiral spring.

Moreover, according to another aspect of the present invention, there is provided a device for delivery of predetermined doses of liquid medicament wherein a cartridge housing is coupled to the outer cover and wherein the interior part of the cartridge housing engaging the plunger rod is provided with means engages longitudinal extending means on the plunger rod and wherein the interior part of the plunger rod driving member engaging the plunger rod is provided with a thread that corresponds to the thread on the plunger rod, so that the rotation of the plunger rod driving member will drive the plunger rod towards the proximal end of the cartridge the predetermined distance without rotation.

Moreover, according to another aspect of the present invention, there is provided a device for delivery of predetermined doses of liquid medicament wherein the interior part of the plunger rod driving member engaging the plunger rod is provided with means that engages longitudinal extending means on the plunger rod, and in that the interior part of the non-rotating bearing is provided with a thread that corresponds to the thread on the plunger rod, so that the plunger rod moves towards the proximal end of the cartridge the predetermined distance with rotation.

Further, according to another aspect of the present invention, there is provided a device for delivery of predetermined doses of liquid medicament wherein a dose setting member is adapted to be rotated in terms of at least one predetermined step when the device is in the medicament non-delivery state for increasing the accumulated energy in the energy accumulating member with at least one step and also adapted to be pulled towards the distal end of the delivery device in order to release the accumulated energy in the energy accumulating member for cancelling a dose.

Moreover, according to another aspect of the present invention, there is provided a device for delivery of predetermined doses of liquid medicament wherein the exterior part of the plunger rod driving member is designed as to in its proximal end be provided with outwardly protruding flanges which are engaged to inward protruding stopper means provided on the interior part of an actuation sleeve when the device is in the medicament non-delivery state.

Further, according to another aspect of the present invention, there is provided a device for delivery of predetermined doses of liquid medicament wherein the outwardly protruding flanges can be designed with a number of dose step protrusions, equally distributed along the circumference of the proximal part of the plunger rod driving member so that every dose step delivers the same predetermined amount of medicament.

Moreover, according to another aspect of the present invention, there is provided a device for delivery of predetermined doses of liquid medicament wherein the device during medicament delivery is adapted to be set in the medicament non-delivery state before the entire set dose has been delivered, whereupon the plunger rod stops its movement towards the proximal end of the cartridge, and that the device thereafter is adapted to be set in the medicament delivery state, whereupon the plunger rod continues to move the predetermined distance towards the proximal end of the device.

According to another aspect of the present invention, there is provided a device for delivery of predetermined doses of liquid medicament wherein the device is adapted to be connected to a medicament administrating member in the form of a mouth or nasal piece, which the patient puts in the mouth or nose, respectively, whereby the predetermined dose of medicament is inhaled by the patient when the delivery device is in the medicament delivery state.

According to another aspect of the present invention, there is provided a device for delivery of predetermined doses of liquid medicament wherein the device is adapted to be connected to a medicament administrating member in the form of a nozzle, whereby the predetermined dose of medicament is sprayed to the eye or onto the skin of the patient when the delivery device is in the medicament delivery state.

According to another aspect of the present invention, there is provided a device for delivery of predetermined doses of liquid medicament wherein the device is adapted to be connected to a medicament administrating member in the form of a member that delivers the predetermined dose of medicament in the form of at least one drop when the delivery device is in the medicament delivery state.

According to another aspect of the present invention, there is provided a device for delivery of predetermined doses of liquid medicament wherein the device is adapted to be connected to a medicament administrating member in the form of a needle for the injection of the predetermined dose of medicament into the body of the patient when the delivery device is in the medicament delivery state.

BRIEF DESCRIPTION OF THE DRAWINGS

FIGS. 1-9 refer to the delivery device according to a first embodiment;

FIG. 1 illustrates the delivery device in a cross-sectional view according to a configuration wherein the plunger rod is adapted to be in a non-driven state during medicament delivery, FIG. 2 illustrates the distal part of the delivery device without the outer cover, the housing member or the coupling spring, FIG. 3 illustrates the delivery device as described in connection to FIG. 2 but including the housing member and the coupling spring, FIG. 4 illustrates the housing member and the flat spiral spring with the proximal end of the housing member facing towards the viewer, FIG. 5 illustrates the housing member and the flat spiral spring, comprised in a spring cover, with the distal end of the housing member facing towards the viewer, FIG. 6 illustrates the connection between the actuation sleeve, a plunger rod driving member and the plunger rod with the proximal end of the actuation sleeve facing towards the viewer, FIG. 7 illustrates a partly cross-sectional view of the distal part of the delivery device according to a configuration wherein the plunger rod is adapted to be in a driven state during medicament delivery and also illustrates a bearing, which is intended to pick up forces acting on the proximal part of the device in the longitudinal direction thereof, FIG. 8 illustrates the plunger rod driving member from FIG. 7 from above, FIG. 9 illustrates a partly cross-sectional view of the distal part of the delivery device according to a configuration wherein dose steps to be delivered are predetermined, FIGS. 10-14 refer to the delivery device according to a second embodiment;

DETAILED DESCRIPTION OF THE PREFERRED EMBODIMENTS OF THE PRESENT INVENTION

Figure 1A:
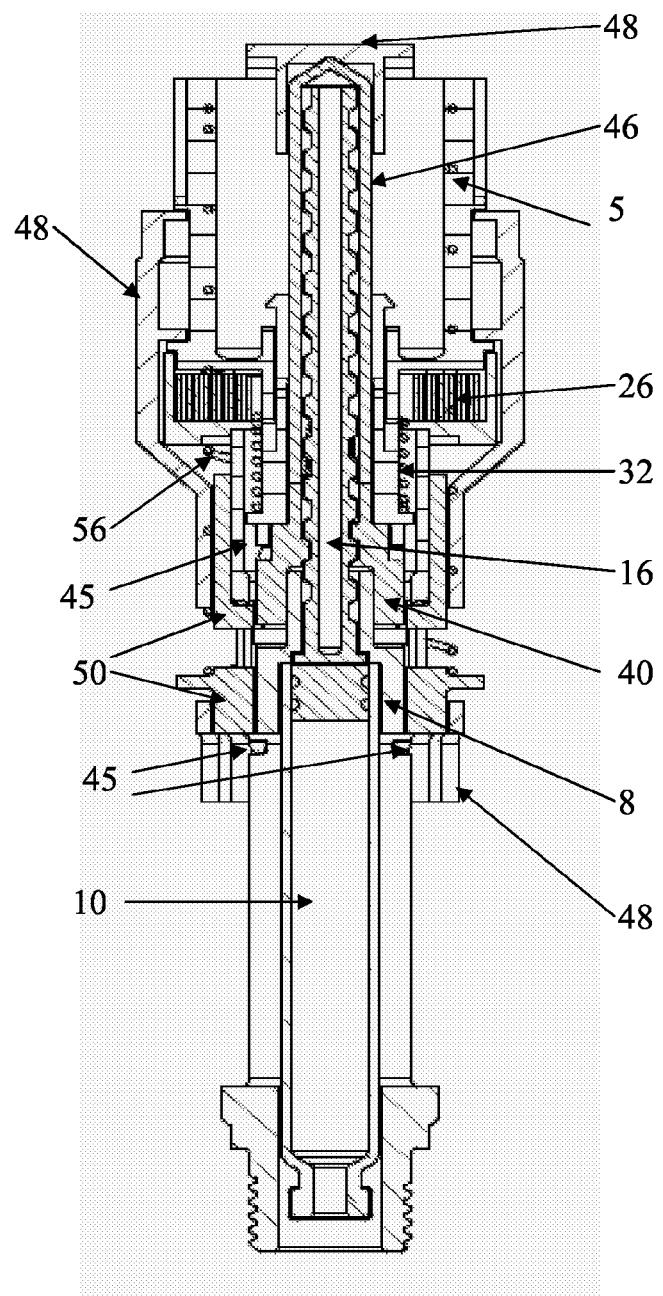
FIG. 1a illustrates the delivery device in a cross-sectional view having an axial bearing, which is intended to pick up forces acting on the proximal part of the device in the longitudinal direction thereof.

In the present application, when the term "distal part/end" is used, this refers to the part/end of the delivery device, or the parts/ends of the members thereof, which under use of the delivery device, is located the furthest away from the medicament delivery site of the patient. Correspondingly, when the term "proximal part/end" is used, this refers to the part/end of the delivery device, or the parts/ends of the members thereof, which under use of the delivery device is located closest to the medicament delivery site of the patient.

The Delivery Device of the Present Invention According to a First Embodiment

FIGS. 1-6 refer to a configuration of the delivery device wherein the plunger rod is adapted to be in a non-rotating state during medicament delivery. The delivery device 2 comprises in its distal end a dose setting member in the form of a dose wheel 4 and in its proximal end a cartridge housing 8, coupled to an outer cover 48, comprising a cartridge 10. The cartridge 10 is intended to be filled with the liquid medicament to be administered to the patient and the delivery device is thus provided with means in order to be connected to a suitable medicament administrating member, provided with corresponding means (not shown). The medicament administrating member is preferably a mouth or nasal piece, which the patient puts in his mouth or nose, respectively, whereby a metered dose of medicament is inhaled by the patient when the delivery device is set in a medicament delivery state, which will be described in further detail below. The medicament administering member can also be a member that introduces the liquid medicament to the eye of the patient, such as a suitable nozzle that sprays the medicament to the eye, or a member that delivers the medicament e.g. to the eye of the patient or in a glass/cup in the form of droplets. Naturally, a nozzle as a medicament administrating member can also be used in order to spray the medicament onto the skin of the patient. The medicament administrating member can also be a needle for the injection of a liquid medicament into the body of the patient, wherein the liquid can have a low as well a high viscosity.

Figure 5:
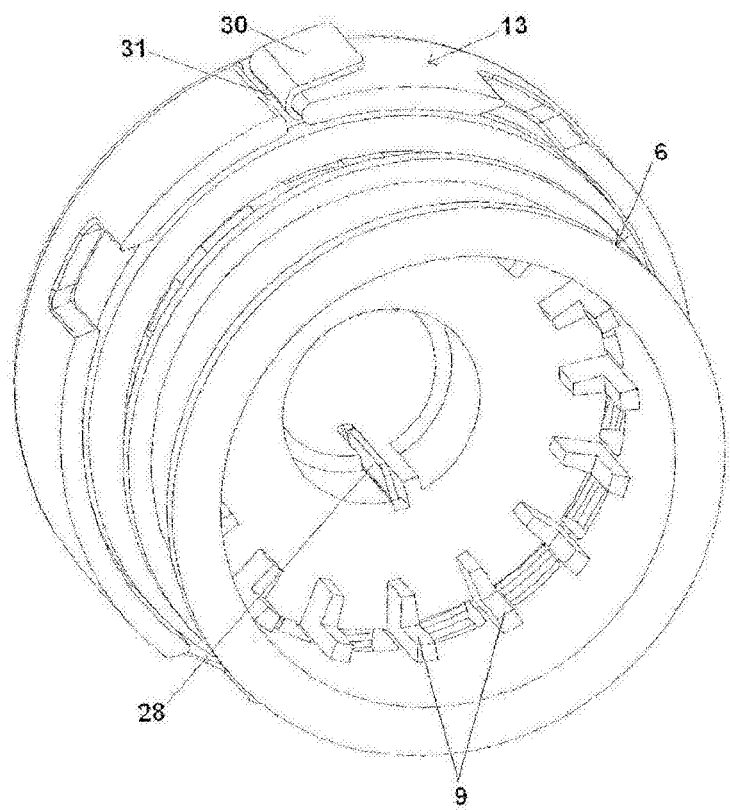
Figure 6:
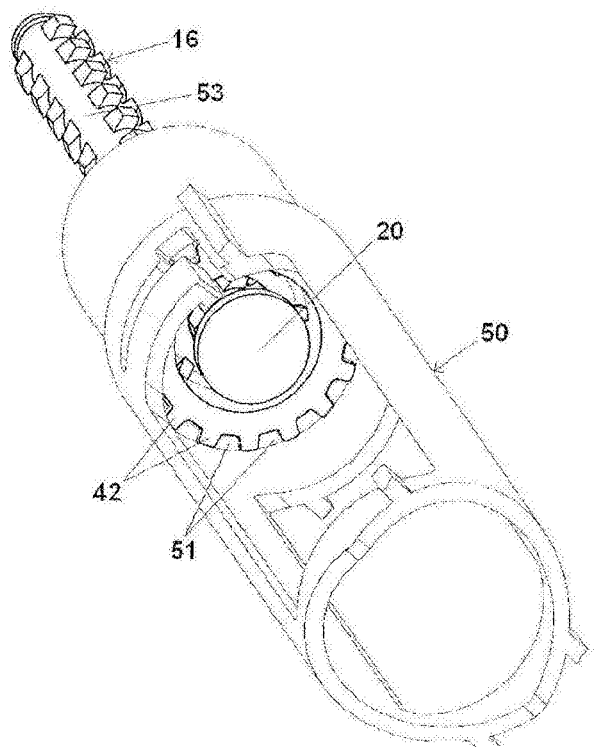

The dose wheel 4 comprises a dose wheel turning member 5 and a member 6 housing the energy accumulating member (see below), which members 5, 6 are adapted in order to be firmly, and removably, connected with each other. For this purpose, as seen in FIGS. 2 and 5, respectively, the exterior of the proximal part of the dose wheel turning member 5 is provided with a number of equally distributed splines 7, which are adapted to engage corresponding inward protruding means 9 of the housing member. Thus, when the splines 7 and the protruding means 9 are engaged, the housing member 6 is rotated along with the turning member 5, when the latter is rotated for instance clock-wise, which will be described in further detail below. When the turning member is pulled towards the distal end of the delivery device, the splines 7 and the protruding means 9 are brought out of engagement and the dose wheel turning member is thus adapted to also release the housing member. The housing member 6 is further provided with a shoulder 11 adapted to be in contact with a corresponding means (not shown) in the outer cover of the device (not shown).

An elongated screw threaded plunger rod 16 is provided in the interior of the delivery device 2, running along the longitudinal axis of said device 2, which device thus is provided with means in order to house such a screw threaded member 16. The plunger rod 16 is in its proximal end provided with a plunger cap 20 adapted to be in contact with a piston 22, which piston 22 is sealingly and slidably provided inside the cartridge 10.

Figure 4:
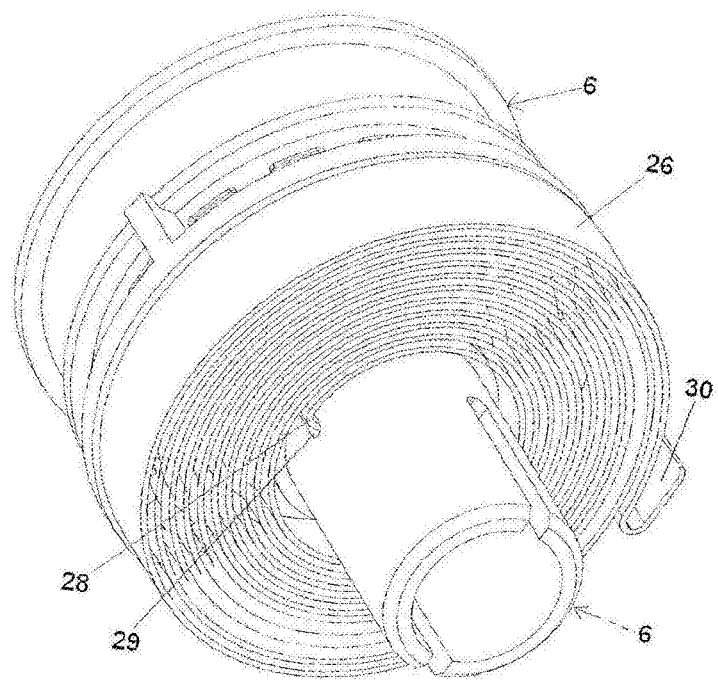

The housing member 6 is adapted to house an energy accumulating member in the form of a flat spiral spring 26, which spring 26 is provided winded in layers around the exterior of the proximal part of the housing member 6, as seen in FIG. 4. The flat spiral spring 26 is in its inner end provided with inner holding means in order to be attached to the housing member 6, such as for instance a protruding member 28 adapted to be fitted with a corresponding slit 29 in the housing member 6, or alternatively a hole of a suitable size in the flat spiral spring 26, and a smaller screw or other similar means for the anchoring of the flat spiral spring 26 in the housing member 6.

At the outer end of the flat spiral spring 26, said flat spiral spring 26 is provided with outer holding means in order to be connected to the flat spiral spring cover 13 of the delivery device 2. Said outer holding means comprises preferably a bend 30 of the outer end of the flat spiral spring 26, which hitches corresponding means 31 in the flat spiral spring cover 13. The cover 13 is provided with means (not shown) in order to be rotationally fixed in the outer cover.

Figure 3:
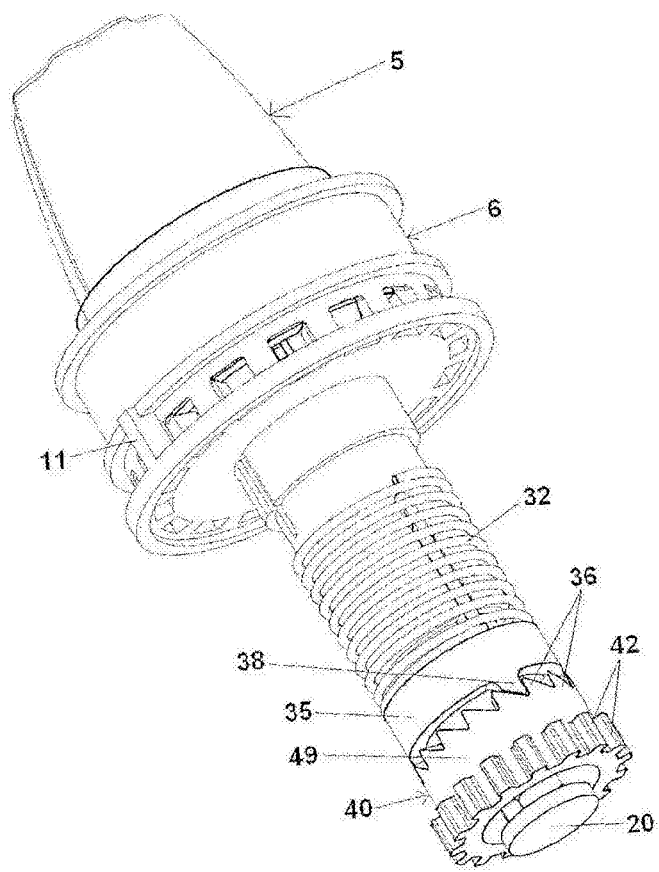

The dose wheel 4 is further in its proximal end adapted to house a coupling member 34, as seen in FIG. 2. Said coupling member is in its proximal end provided with a crown 35, which proximal end in turn is provided with at least one, preferably two equally distributed, bevelled protrusions 38. The crown 35 of the coupling member 34 is adapted to engage a plunger rod driving member, in the form of a nut 40. Herein the term nut is defined as a member provided with a through going hole, such that the interior of the member is provided with a thread of predetermined pitch of grooving, i.e. a pre-determined screw pitch, said member is thus adapted to be screw threaded on a second member provided with a corresponding thread. The nut 40 is in this case adapted to engage with the plunger rod 16, i.e. the interior of the nut 40 is provided with grooves of a predetermined pitch in order to be screw threaded on the plunger rod 16. The nut 40 is designed as to in its proximal end be provided with outwardly protruding flanges 42 and in its distal end be provided with a skirt 49, the distal end of which is provided with a number of equally distributed bevelled recesses 36, which correspond to the protrusions 38 of the crown 35. The coupling member is further provided with a helical coupling spring 32, which proximal end is in contact with the distal end of the crown 35, as seen in FIG. 3. The distal end of the coupling spring 32 is firmly fixed to the coupling member.

When the delivery device 2 of the first embodiment is in a locked state, i.e. a non-medicament delivery state, as will be described in further detail below, the nut 40 is held in a locked non-rotatable state by means of an actuation sleeve 50. The interior of said sleeve 50 is for this purpose provided with inward protruding stopper means 51, adapted to be provided in between the protruding flanges 42 of the nut 40, see FIG. 6. The actuation sleeve 50 is further adapted to, preferably at is proximal end, engage a dose actuation member 44, and is at its distal end provided with means in order to be connected to a helical actuation spring 56, said spring 56 is provided surrounding the distal end of the actuation sleeve and the distal end of the actuation spring 56 is in contact with the dose wheel 4, as seen in FIG. 1.

Figure 7:
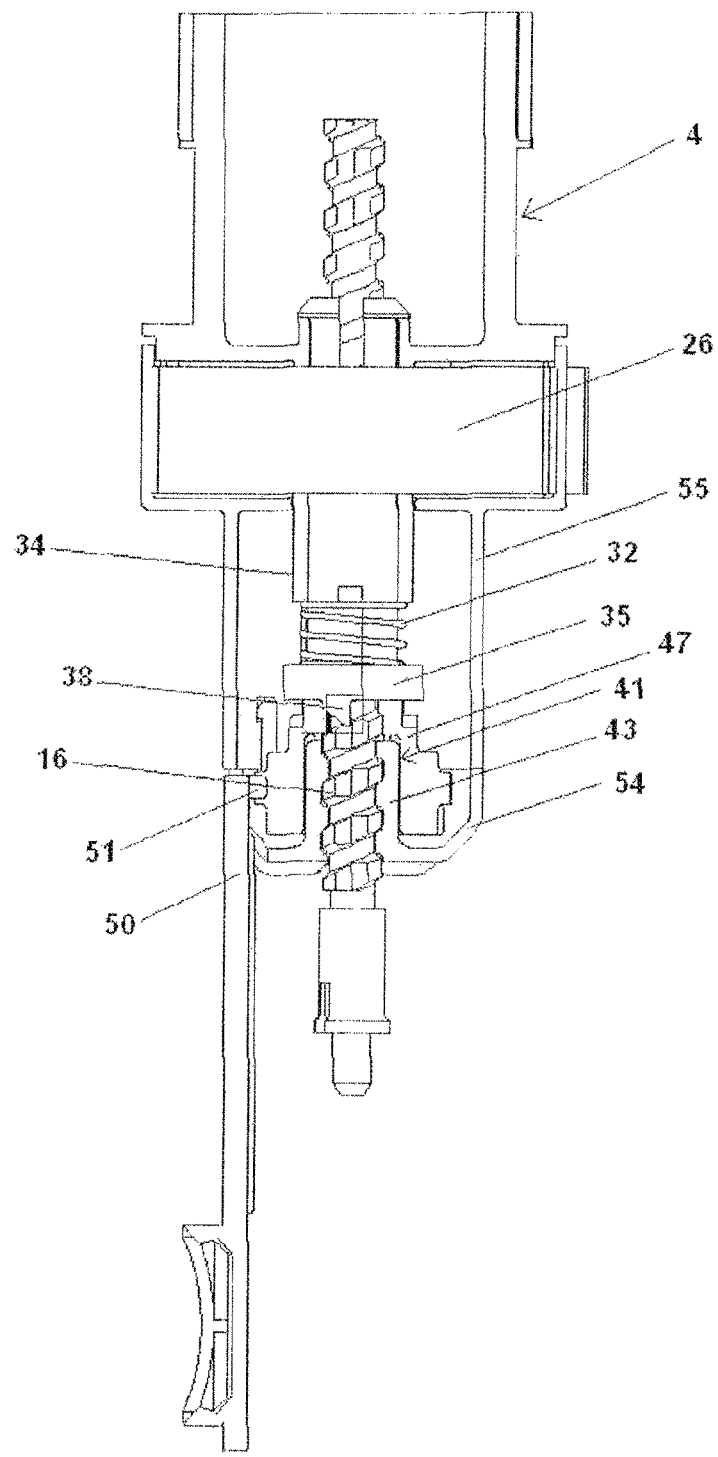
Figure 8:
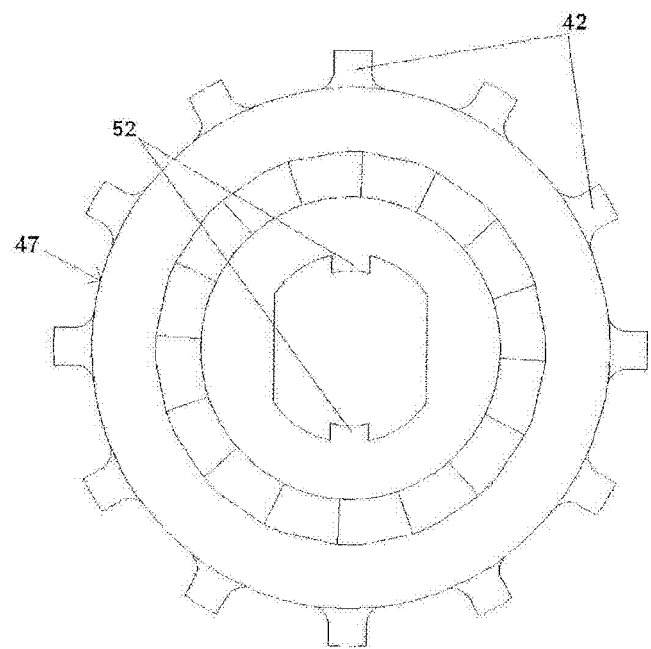
Figure 9:
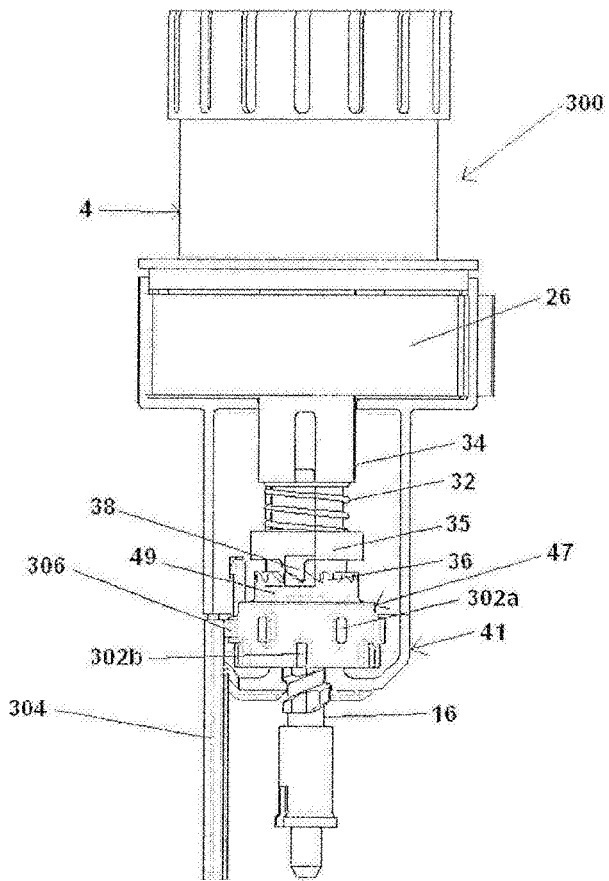

FIGS. 7-9 refer to a configuration of the delivery device according to the first embodiment, wherein the plunger rod is adapted to be in a rotating state during medicament delivery. Hence, the above described refers to a configuration, wherein the plunger rod is adapted to be in a non-rotating state during medicament delivery. However, the two configurations coincide in most of their respects. The main difference between said configurations is within the plunger rod driving member. This will be described in further detail below and also in connection with the preferred use of the delivery device according to the first embodiment.

In the plunger-rod-rotating-state-configuration of the delivery device 2, a non-rotating bearing 41 is partly provided in between a plunger rod driving member 47 and the plunger rod 16. In FIG. 7, the driving member 47 and the bearing 41 are seen in cross section which is not the case for the coupling member 34. Also in the plunger-rod-rotating-state-configuration, the bevelled protrusions 38 of the coupling member are adapted to abut against bevelled recesses 36 of the driving member 47. This is not seen in FIG. 7, due to the cross-sectional view of the member 47. However, even if not shown in FIG. 7, the plunger rod driving member 47 has a skirt 49 provided with recesses 36 just like the plunger rod driving member 40. The protrusions 38 and the recesses 36 are adapted to cooperate substantially in the same way also in the plunger-rod-rotating-state-configuration. That is, the distal part of the plunger rod driving member 47, has the same appearance and function as the plunger rod driving member 40 also in the plunger-rod-rotating-state-configuration.

However, in the plunger-rod-rotating-state-configuration, the through going hole provided in the plunger rod driving member 47, can be said to comprise two sections; a distal section and a proximal section, wherein the distal section has a diameter that is smaller than the diameter of the proximal section. The plunger rod driving member 47 thus comprises a distal part and a proximal part, corresponding to the distal and proximal sections, respectively, of the hole. The interior of the distal part of the plunger rod driving member 47 is provided with interior means 52, see FIG. 8, that are adapted to set the plunger rod in a rotating state, i.e. the means 52 corresponds to longitudinal extending means 53 on the rod 16. The means 52 are thus adapted to travel along the longitudinal axis of the rod 16. The interior of the proximal part of the driving member 47 is provided with a substantially flat surface. In the plunger-rod-rotating-state-configuration, only the distal part of the plunger rod driving member 47 is adapted to engage the plunger rod. The proximal part of the driving member 47 is adapted to house an interior part of the bearing 41.

The bearing 41 is a fix non-rotating member, having an interior tubular formed part 43 which is housed within the proximal part of the driving member 47. In between the outer surface of the tubular formed part 43 and the interior of the proximal part of the plunger rod driving member 47 is an air gap provided since the components are adapted to be rotated relative to each other. The interior of the tubular formed part 43 of the non-rotating bearing is provided with a thread of a predetermined screw pitch that corresponds to the thread on the plunger rod. That is, as will be described in greater detail below, the rod is urged towards the proximal part of the device in a rotating state while the bearing remains fix. The contact point between the proximal end of the plunger rod and the plunger cap 20, is thus in the plunger-rod-rotating-state-configuration provided with means (not shown), such that the proximal end can rotate substantially without friction losses at said contact point. The bearing 41 has preferably an outer part 54 connected to an outer cover 55. In this way, the bearing 41 can effectively pick up forces acting on the proximal part of the device in the longitudinal direction thereof.

As further seen in FIG. 7, the actuation sleeve 50 of the plunger-rod-rotating-state-configuration is provided with a stopper means 51 that is adapted to cooperate with external means 42 on the outer surface of the proximal part of the plunger rod driving member 47. When the stopper means 51 of the plunger-rod-rotating-state-configuration engages the means 42, the driving member 47 is held in a non-rotating state, and consequently, when the stopper means 51 releases the means 42, the driving member 47 is set in a rotating state. Even if not shown in FIG. 7, the stopper means 51 and the means 42 of the plunger-rod-rotating-state-configuration, can have the same appearances and functions as described in connection with the plunger-rod-non-rotating-state-configuration. Moreover, even if no actuation spring 56 is shown in FIG. 7, such a spring can naturally be present also in the plunger-rod-rotating-state-configuration.

The Delivery Device of the First Embodiment and the Function Thereof, Will Now be Explained in Detail According to a Preferred Use Thereof The predetermined dose is in a first dose delivery step set by the use of the dose wheel 4, with the use of which the dose is increased by predetermined equally large dose increment steps. One predetermined dose increment step, corresponds to a clock-wise rotation of the dose wheel 4 with one step, which step corresponds to a predetermined number of degrees. Thus, with each dose increment step, the dose wheel turning member 5 is turned clock-wise an additional step corresponding to said predetermined number of degrees.

So, in order to set a predetermined dose that corresponds to for instance two dose increment steps, the dose wheel turning member 5 is turned clock-wise two steps.

When the dose wheel turning member 5 is rotated, the housing member 6 and the coupling member 34 will rotate correspondingly and hence also the inner holding means 28, 29 of the flat spiral spring 26. Also the shoulder 11 of the housing member 6 will be brought out of engagement with the corresponding means of the outer cover when the housing member 6 is rotated clock-wise.

When the coupling member 34 rotates clock-wise, the protrusions 38 will move along the bevelled edge of the recesses 36 of the plunger rod driving member 40;47, with which recesses 36 the protrusions are initially in engage with, and the coupling member will thus move towards the distal end of the delivery device 2, compress the coupling spring 32, and unlock the dose wheel from the plunger rod driving member 40;47. The flat spiral spring 26 is hereby free to wind up and accumulate energy corresponding to the rotation of the dose wheel turning member 5 the number of degrees corresponding to one clock-wise step turn. Due to the power accumulated in the compressed coupling spring 32, the coupling member 34 will now move back towards the proximal end of the delivery device 2 when the protrusions 38 climbs over the edge of the bevelled recesses 36 and lock the coupling member 34 as well as the dose wheel 4 to the plunger rod driving member 40;47, when the protrusions 38 engage the recesses 36 following the recesses it was previously in engagement with. The dose wheel turning member 5 is turned the additional and final step, whereby the above described procedure is repeated. The flat spiral spring 26 has thus after the completion of the first dose delivery step, accumulated the energy that corresponds to the rotation of the dose wheel turning member 5 the number of degrees corresponding to a two step clock-wise turn.

The delivery device 2 is now ready to deliver the predetermined dose corresponding to two dose increment steps, i.e. the delivery device 2 is now ready to be set in a medicament delivery state. This is accomplished by in a second dose delivery step, activate, i.e. pushing, the dose actuation member 44 in the direction as indicated by the arrow A in FIG. 1. When the dose actuation member 44 is activated, said member 44 will push the actuation sleeve 50 towards the distal end of the device 2, whereby the protruding stopper means 51 of the actuation sleeve 50 and the external means 42 of the plunger rod driving member 40;47 are brought out of engagement and the plunger rod driving member 40;47 is released for rotation. In an alternative embodiment, the means that releases the plunger rod driving member 40;47 for rotation can be a breath sensing means (not shown), i.e. the plunger rod driving member 40;47 is released for rotation by means of the inhalation of the user. If the delivery device 2 is intended to be used as an injection device, the pushing of the proximal end of the actuation sleeve 50 against the patient's skin at the medicament delivery site will have the same function as the dose actuation member 44.

Due to the energy accumulated in the flat spiral spring 26 in the first dose delivery step, the coupling member 34 and the plunger rod driving member 40;47 will due to the output torque of the spring 26 when said spring now is free to unwind, rotate counter clock-wise the number of degrees corresponding to the two step turn.

If the user wants to cancel a dose, the turning member must be pulled towards the distal end of the delivery device, wherein the splines 7 and the protruding means 9 are brought out of engagement and the dose wheel turning member is thus adapted to release the housing member.

In the plunger-rod-non-rotating-state-configuration, the rotation of the plunger rod driving member 40 will drive the plunger rod, and due to non-rotating interior means provided in the cartridge housing (8; 101) adapted to engage a longitudinal extending means (53; 131) on the plunger rod so that the plunger rod moves towards the proximal end of the cartridge the predetermined distance without rotation. The finer the pitch of grooving, i.e. the finer the screw pitch in the interior of the driving member 40, i.e. the finer the pitch of grooving of the thread on the rod, the higher the force provided to the piston, when the rod in this case is urged linearly without rotation into the cartridge. Further means to bring more of spring force to an efficient output torque, is to reduce the friction between the driving member and its backing support, for instance by means of low friction washer, lubricant(s) or a ball bearing or by using low friction material in the nut and/or the plunger rod.

Figure 1B:
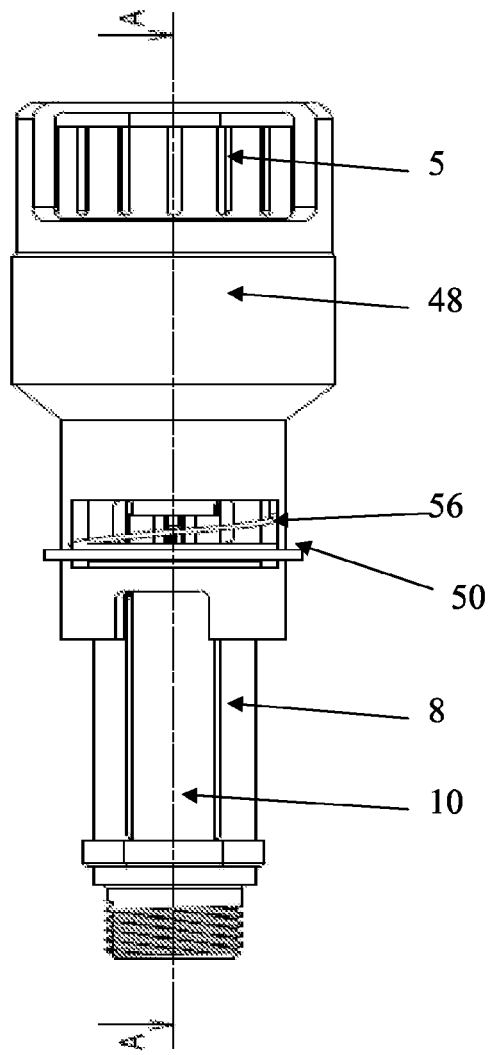
FIG. 1b illustrates the distal part of the delivery device with the outer cover.

In the plunger-rod-non-rotating-state-configuration the plunger rod driving member 40 is preferably connected to an axial bearing 46 extending along the plunger rod 16 as seen in FIG. 1*a*. The distal part of the bearing 46 has preferably ending in a point supported on an outer cover 48 and the cartridge housing 8 is coupled to the outer cover 48 through a sleeve means 45. In this way, the axial bearing 46 can effectively pick up forces acting on the proximal part of the device in the longitudinal direction thereof.

In the plunger-rod-rotating-state-configuration, when the plunger rod driving member 47 is rotated due to the output torque of the spring 26, this will rotate also the plunger rod 16 due to the interacting of the means 52 and 53. Due to the threaded interior of the bearing 41 that engages the rod 16, said rod is further urged towards the proximal part of cartridge with a rotating movement the predetermined distance towards the proximal end into the cartridge 10. The finer the pitch of grooving, or screw pitch, in the interior of the bearing 41, i.e. the finer the pitch of grooving of the thread on the rod, the higher the force provided to the piston, when the rod in this case is urged with rotation into the cartridge. In the plunger-rod-rotating-state-configuration, all friction is substantially between the plunger rod and the interior of the part 43. Thus, the friction between the driving member 47 and its backing support is reduced.

In any configuration, the device 2 is designed in accordance with the cartridge 10 so that the movement of the piston 22 the predetermined distance towards the proximal end of the cartridge 10, will correspond to the delivery of the dose set in the first dose delivery step corresponding to two dose increment steps. The dose wheel 4 will rotate back to its original position when the plunger rod driving member 40;47 and the coupling member 34 is rotated during medicament delivery. The device 2 is further provided with means (not shown) that will visualize the delivered dose for the user by counting down the set dose increments. The circumferential surface of for instance the housing member 6 is preferably provided with suitable numerical indicators that are visible for the user through a window (not shown) provided in the outer cover, visualizing the dose to be delivered. The window can optionally be provided with a suitable lens or the like, in order to enlarge the dose indicators for the user. Naturally, the set dose is also visual for the user through the dose window during the first dose delivery step, as for each such step, either by using one default dose setting (described below) or varying it between doses.

When the predetermined dose has been delivered and the user of the delivery device 2 releases the dose actuation member 44, the actuation sleeve 50 will, due to the power accumulated in the actuation spring 56 when the actuation sleeve is pushed towards the distal end of the device 2, move back to its original position and once again lock the plunger rod driving member 40;47 for rotation. The plunger rod 16 will stay at its current position, with its proximal end in contact with the piston 22, and the delivery device 2 is ready to be used again. If the device is used as an injection device, the removal of the device from the medicament delivery site, i.e. the injection site, will thus cause the actuation sleeve 50 to move back to its original position, and hence temporarily or permanently stop the medicament delivery, and if provided with breath sensing means in an inhaler type of device as described above, the user may simply stop his inhalation. If the cartridge is emptied before the set dose is delivered, the dose remaining to be delivered is visualized for the user.

The user of the delivery device can also release the dose actuation member (stop his inhalation, or for injectors remove the device from the injection site), during medicament delivery and hence set the delivery device in the medicament non-delivery state before the set dose has been delivered. The user can then once again activate the dose actuation member (start to inhale, or for injectors push the proximal end of the actuation sleeve against the patient's skin), whereby the set dose continues to be delivered. The procedure above can be repeated an optional number of times until the entire set dose has been delivered. This procedure may be suitable when the patient for instance is to inhale a large predetermined volume of medicament and wants to divide the medicament delivery into multiple inhalation steps, or wants to inject a predetermined volume of medicament at different injection sites.

It is also possible to provide the device with means (not shown) that sets a certain dose as a default dose value, for instance by providing at least one of the bevelled recesses 36 with a stopper means, that will prevent the protrusions 38 from slide over the recess provided with said stopper means. This will thus prevent the user from rotating the dose wheel turning member further than the number of degrees corresponding to the default dose value, when the stopper means is provided at a recess corresponding to the rotation of the dose wheel turning member the desired number of degrees.

In the currently preferred design of the present invention according to the first embodiment, the cartridge 10 is a 1.5 ml ISO standard cartridge. The flat spiral spring 26 is in the currently preferred embodiment made of SS 2331 stainless steel, has a thickness of 0.3 mm, a width of 4.5-5.1 mm, and an arbor diameter of 11 mm. The number of coils of the flat spiral spring 26 is 9 turns. These flat spiral spring characteristics will give rise to an output torque of the flat spiral spring 26 in the range of 40-54 Nmm, which output torque will give rise to an operating force on the piston in the order of 27-36 N, depending on the threaded configuration of the plunger rod, i.e. the predetermined pitch of grooving of the thread on the rod, in the currently preferred design 4.3 mm/turn. The flat spiral spring 26 has further preferably no stack friction and no stick-slip and thus no lubrication of the spring 26 is needed.

Moreover, in the currently preferred design, the dose increment steps are in the order of 0.01 ml per step, and it is possible to set a dose in the range of 0.01-0.1 ml. One dose increment step of 0.01 ml, corresponds to a clock-wise rotation of the dose wheel 4 with 22.5°. Thus, the minimum dose to be delivered, i.e. 0.01 ml, corresponds to a turn of the dose wheel 4 with 22.5° and the maximum dose to be delivered, 0.1 ml, corresponds to a turn of the dose wheel with 225°.

However, the user of the device can helically pull the dose setting member towards the distal end of the device during setting of the dose to be delivered, so that the shoulder 11 is brought out of engagement with the outer cover. The flat spiral spring can thus wind up a number of coils exceeding the above described in order to accumulate more energy and thus provide for a larger dose to be delivered.

Thus, in the example described above with the delivery of a dose corresponding to two dose increment steps, the dose wheel 4 is in the first dose delivery step turned clock-wise 45°. The flat spiral spring 26 thus winds up and obtains the energy that corresponds to a 45° clock-wise turn of the dose wheel turning member 5. The later counter clock-wise rotation of the plunger rod driving member 40;47 with 45° will drive the plunger rod 0.54 mm towards the proximal end into the cartridge 10. The movement of the piston 22 towards the proximal end of the cartridge 10 with a distance of 0.54 mm, will correspond to the delivery 0.02 ml of the liquid medicament.

Figure 15:
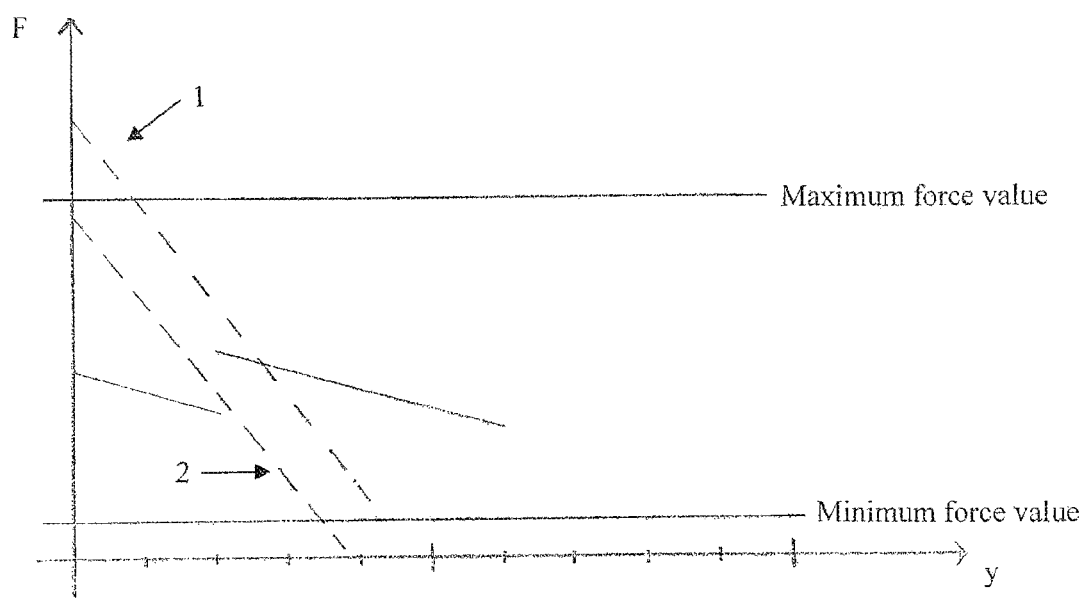
FIG. 15 illustrates graphically the force acting on the piston as a function of the traveled distance by the piston during medicament delivery in comparison with prior art devices (not to scale).

So, with the present invention according to the first embodiment, the force that drives the plunger rod with or without rotation towards the proximal end of the delivery device due to output torque of the flat spiral spring that rotates the plunger rod driving member 40, 47 is in an effective way to set a predetermined force value during the first dose delivery step, due to the interacting of the energy accumulating member and the predetermined pitch of grooving, or screw pitch, of the thread on the rod and its interacting components. This set force and the force that acts on the piston is during the entire medicament delivery ensured to be above or equal to a minimum force value, which is the lowest force value needed to deliver the set predetermined dose, and is also ensured to be below a maximum force value, which is the first force value at which it exists a risk of damaging the cartridge. FIG. 15 graphically shows the force acting on the piston (F) as a function of the traveled distance (y) by the piston from its original position during medicament delivery, wherein the delivery device first delivers a predetermined dose corresponding to two dose increment steps and thereafter delivers a dose corresponding to four dose increment steps, the indications on the y-axis thus correspond to the dose increment steps. The inclination of the continuous lines, respectively, is identical. As seen, the force is during medicament delivery above and below, respectively, said minimum and maximum force value and the force is thus within a predetermined range. It is to be understood that the force curve obtained with the inventive device according to the first embodiment can have different appearances depending on the type of spring chosen as the energy accumulating member. If for instance a substantially constant force is desired to be applied to the piston, a spiral spring resulting in such a force can easily be provided in the device by the person skilled in the art. The dashed lines 1 and 2 represent the force acting on the piston in a prior art delivery device provided with a helical spring as described by ways of introduction, during the delivery of an amount of medicament corresponding to four dose increment steps. With reference to dashed line 1, the initial force acting on the piston needs to be over the maximum force value in order for the piston to reach the distance in the cartridge that delivers a dose corresponding to four dose increments steps, i.e. there is a risk of damaging the cartridge. If the initial force is lowered, as seen when turning to the dashed line 2, the force acting on the piston will decrease to value below the minimum force value before the piston has reached its required position inside the cartridge and there is a risk that the piston will get stuck before the entire set dose is delivered. Thus, with the present invention, the predetermined dose is ensured to be delivered and the risk for damaging the cartridge or the device due to a too high initial force acting on the piston is substantially reduced, which is a problem with prior art automatic medicament delivery devices.

Moreover, with the present invention according to the first embodiment, there is no longer a need for a pre-tensed helical spring to be provided at high tensioning in the interior of the delivery device in order to provide the plunger rod with a force for driving said rod inside the cartridge, in a way that is critical to components that are important for the dose and the dose-to-dose accuracy. Hence the problem with creep in the plastic materials of the delivery device due to tensions provided by the pre-tensed spring, as discussed above, is effectively and substantially reduced. The problem with plastic deformation is also reduced due to the fact that the force that is applied to the plunger rod does not need to be initially high as with the prior art devices, due to the effective cooperation between the energy accumulating member and the threaded plunger rod of the present invention. That is, having an output torque of a flat spiral spring rotating a plunger rod driving member and having a plunger rod provided with a thread of a predetermined screw pitch, requires less force to act on the piston in comparison with prior art devices. Particularly if friction is reduced by means of for instance low friction washers, lubricant(s), a ball bearing or by using low friction material in the plunger rod and its interacting components However, even though the present invention according to the first embodiment has been described and illustrated in detail, said description and said illustrations shall be regarded as being non limited, since it will be appreciated that only the currently preferred embodiment has been shown. Thus the skilled person is fully capable to modify the teachings of the present invention according to the first embodiment and thus end up with for instance predetermined dose increment steps, and thus a predetermined delivery dose, in different ranges than described above, and also with different cartridge and flat spiral spring characteristics. Also, the skilled person is fully capable to replace the flat spiral spring with other types of energy accumulating members, such as other types of springs capable of providing an output torque. Moreover, the rotation directions mentioned above, can naturally be the opposite rotation direction by suitable configurations of the device that are readily carried out by the person skilled in the art, so that a counter clock-wise rotation as mentioned above instead is a clock-wise rotation, and vice versa.

The Delivery Device of the Present Invention According to a Second Embodiment

Figure 10:
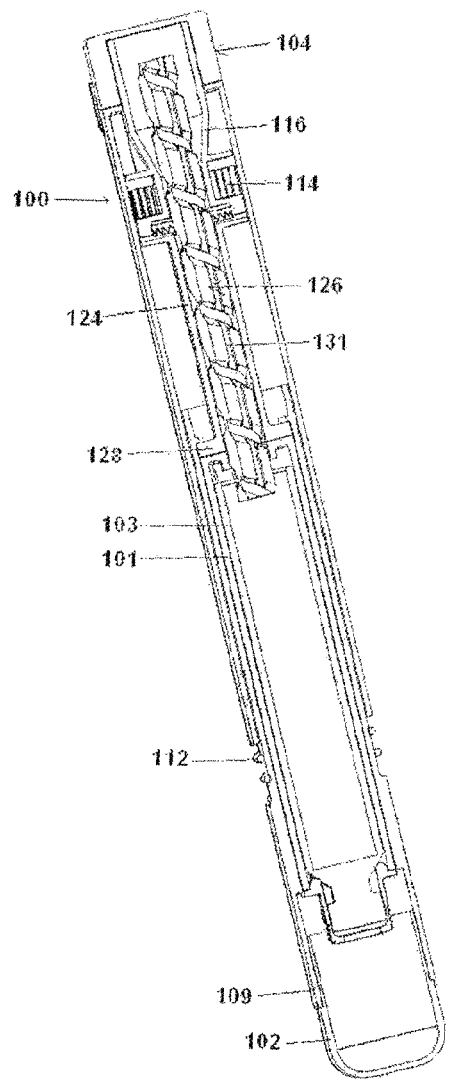
FIG. 10 illustrates the delivery device in a cross-sectional view.
Figure 11:
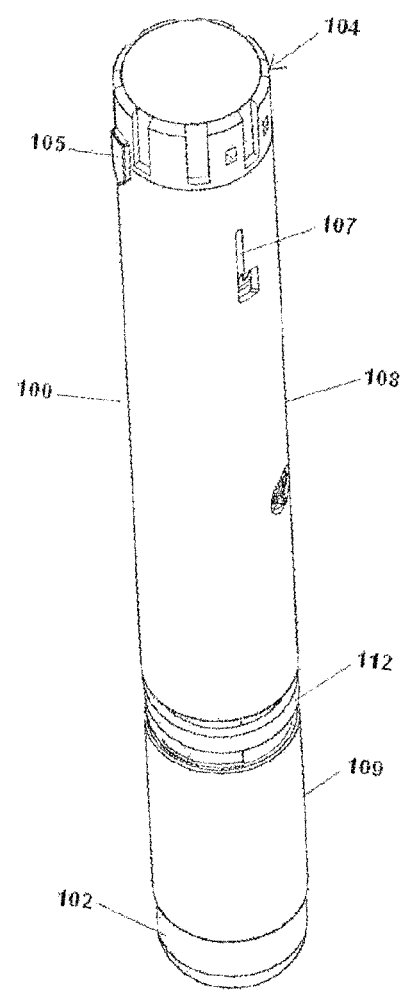
FIG. 11 illustrates an elevation view of the device.

The delivery device 100 of the second embodiment, shown in FIGS. 10-14, comprises in its proximal part a cartridge housing 101, coupled to an outer cover 108, comprising a cartridge 103, as seen in FIG. 10. The cartridge 103 is intended to be filled with the liquid medicament to be administered to the patient and the delivery device is thus provided with means in order to be connected to a suitable medicament administrating member, provided with corresponding means (not shown). The medicament administrating member is in the second embodiment of the present invention preferably a needle for the injection of a liquid medicament into the body of the patient, wherein the liquid can have a low as well as high viscosity, but may also be for instance be a mouth or nasal piece, which the patient puts in his mouth or nose, respectively, whereby a metered dose of medicament is inhaled by the patient when the delivery device is set in a medicament delivery state, which will be described in further detail below. The medicament administering member can also be a member that introduces the liquid medicament to the eye of the patient, such as a suitable nozzle that sprays the medicament to the eye, or a member that delivers the medicament e.g. into the eye or in a glass/cup in the form of droplets. Naturally, a nozzle as a medicament administrating member can also be used in order to spray the medicament onto the skin of the patient.

The delivery device 100 is further in the preferred embodiment provided with a needle shield or actuation sleeve 109, the proximal end of which extends beyond the proximal ends of the cartridge components 101, 103 in order to protect the needle. For further protection of the delivery device, said device may also in its proximal end be provided with removable cap 102. The distal end of the needle shield is provided with inward protruding stopper means 111, the function of which will be described in further detail below. The needle shield is further in its distal end provided with a helical needle shield spring 112, said spring 112 being comprised between the needle shield 109 and an outer device cover 108.

The delivery device comprises further in its distal end, a dose setting member in the form of a dose wheel turning member 104 connected to a member 116 housing an energy accumulating member. The turning member 104 is further provided with a dose indicating member 105, the function of which is to point out the set dose/dose to be delivered (as described in further detail below). The set dose/dose to be delivered is preferably provided as numerical indicators (not shown) printed on the outer cover 108.

The housing member 116 is adapted to house an energy accumulating member in the form of a flat spiral spring 114, said flat spiral spring being provided winded in layers around the housing member. The flat spiral spring is in its inner end provided with inner holding means (not shown) in order to be attached to the housing member 116, such as for instance a protruding member of the flat spiral spring adapted to be fitted with a corresponding slit in the housing member 116 or alternatively a hole of a suitable size in the flat spiral spring, and a smaller screw or other similar means for the anchoring of the flat spiral spring in the housing member 116.

Figure 12:
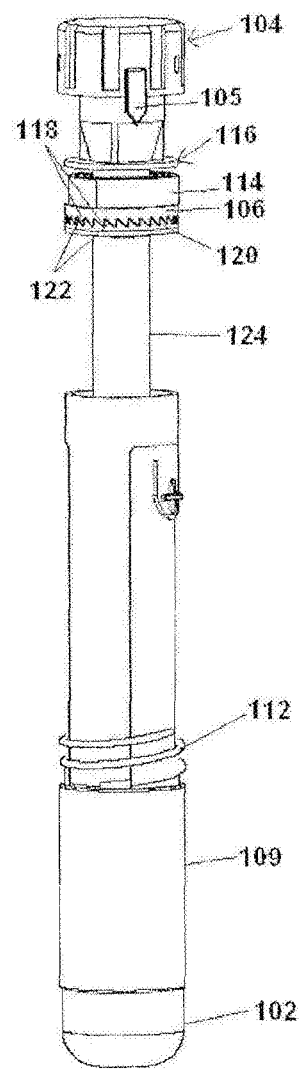
FIG. 12 illustrates the delivery device as described in connection to FIG. 11 but without the outer cover.
Figure 13:
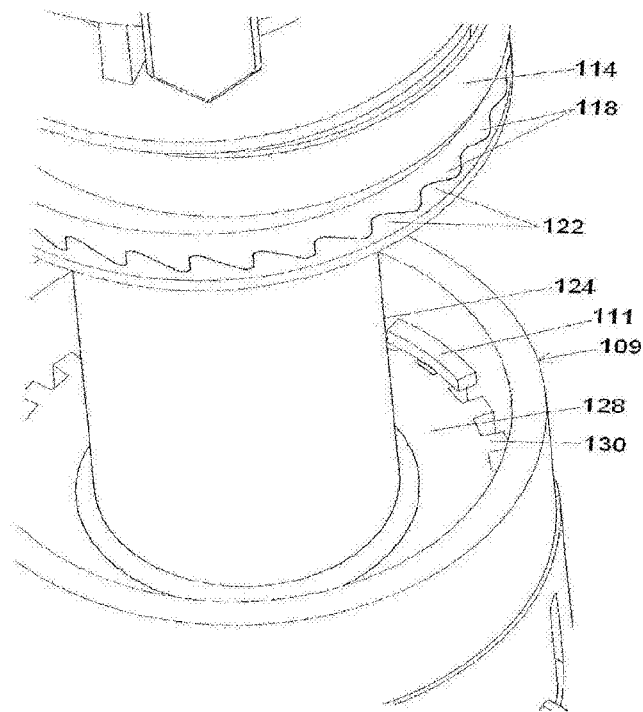
FIG. 13 illustrates an enlarged view of the connection between the needle shield and the plunger rod driving member when the device is in a medicament non-delivery state.

At the outer end of the flat spiral spring 114, said flat spiral spring is provided with outer holding means (not shown) in order to be connected to the outer cover 108 of the delivery device 100. Said outer holding means comprises preferably a slit 107 in the outer cover 108, which engage corresponding means of the end of the flat spiral spring. As seen in FIG. 12, the housing member 116 is further in its proximal end provided with a crown 106 with a number of equally distributed bevelled protrusions 118. Said protrusions 118 thus protrude towards the proximal end of the device.

The protrusions 118 of the crown 116 is adapted to be in contact with protruding bevelled teeth 122 provided equally along the circumference of a rotatable first wheel 120, said teeth 122 thus protrude towards the distal end of the device. The wheel 120 is adapted to be screw threaded on a threaded elongated plunger rod 126 which runs in the interior of the device along the longitudinal axis of said device. The proximal end of the plunger rod 126 is in contact with a piston (not shown) provided sealingly and slidably in the cartridge.

The wheel 120 is connected to a plunger rod driving member in the form of a second wheel 128 via a tubing 124, such that the second wheel 128 is provided proximal to the wheel 120. The second wheel 128 is thus also adapted to be screw threaded on the plunger rod, which is provided in the interior of the tubing 124. The interior of the wheels 120, 128 are thus provided with grooves of a predetermined pitch, i.e. a predetermined screw pitch that corresponds to the thread of the plunger rod. The interior of the tubing 124 is provided with means in order to house the screw threaded plunger rod. The second wheel 128 is provided with outwardly protruding flanges 130. The flanges 130 are adapted to engage the needle shield stopper means 111, such that a stopper means 111 is provided in between two protruding flanges 130 holding the second wheel 128 in a non-rotating state when the delivery device 100 is in a non-medicament delivery state (FIG. 13) which will be described in further detail below.

Also the device of the second embodiment is adapted to be in a plunger-rod-rotating-state-configuration, wherein the plunger rod is urged towards the proximal end of the cartridge with a rotating movement. Hence, the above described refers to a configuration, wherein the plunger rod is adapted to be in a non-rotating state during medicament delivery. However, as in the first embodiment of the delivery device, the two configurations coincide in most of their respects, wherein the main difference between said configurations is within the plunger rod driving member. This will not be described in further detail below since having the teaching above referring to the plunger-rod-rotating-state-configuration of the first embodiment at hand, the skilled person can readily accomplish such a configuration also of the second embodiment, i.e. providing the interior of the wheels 120 and 128 with interior means that rotate the plunger rod, see means 52 of the first embodiment, and providing a non-rotating bearing in the interior of the device, which bearing is provided with an interior thread that corresponds to the thread on the plunger rod, see member 41 of the first embodiment.

The Inventive Delivery Device of the Second Embodiment and the Function Thereof, Will Now be Explained in Detail According to a Preferred Use Thereof Before use, the cap 102 is removed from the device 100 and a suitable medicament administrating member is attached to the cartridge retainer, preferably a needle. Then the dose is set in a first dose delivery step by rotating the dose wheel turning member 104 in clock-wise direction with predetermined equally large dose increment steps. When the turning member is rotated, the housing member 116 rotates as well, whereupon the protrusions 118 slide over the bevelled teeth 122 of the first wheel 120, i.e. when the turning member is rotated a protrusion 118 comes in engagement with the tooth that follows the tooth that said protrusion was previously in engagement with—Each time a protrusion 118 slides over a tooth 122, the dose is increased by one step and the increase of the dose with one step corresponds to a clock-wise rotation of the turning member with a predetermined number of degrees. The set dose is indicated for the user by means of the dose indicating member 105, which points out the set dose, provided printed as numerical indicators printed along the circumference of the exterior surface of the outer cover 108, as described above.

Each time the housing member is rotated clock-wise by one step, the flat spiral spring 114, winds up and accumulates energy that corresponds to the rotation of the dose wheel turning member 104 the number of degrees that corresponds to one clock-wise step turn.

It is also possible to provide the device with means (not shown) that sets a certain dose as a default dose value, for instance by providing the exterior surface of the outer cover with a stopper means at the numerical indicator corresponding to the default dose value, which stopper means will engage the dose indicating member 105, which thus prevents the user to rotate the dose wheel turning member 104 further than the number of degrees corresponding to the default dose value.

If the delivery device needs to be reset, for instance if the user by mistake sets a too high dose, this is accomplished by pulling the dose wheel turning member 104 towards the distal end of the device, such that the protrusions 118 will be brought out of engagement with the first wheel 120, whereby the dose wheel turning member can be rotated back.

Figure 14:
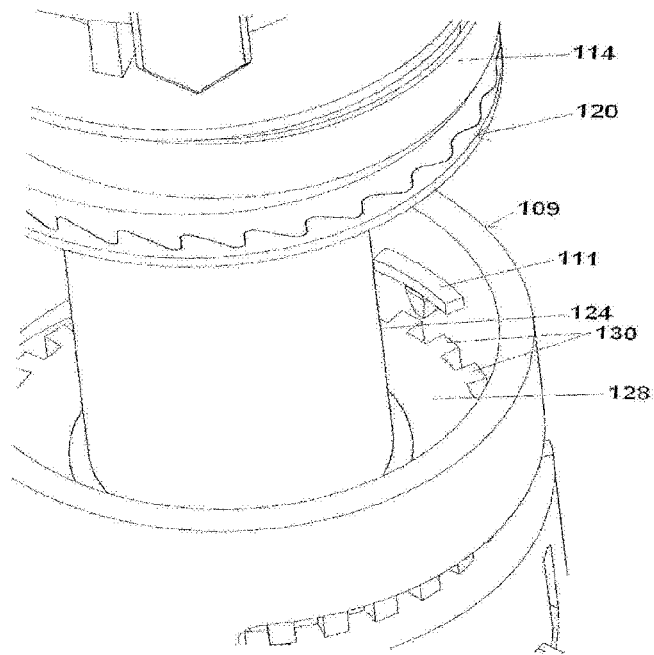
FIG. 14 illustrates an enlarged view as described in connection to FIG. 13 but when the device is in a medicament delivery state.

The delivery device 100 is now ready to in a second dose delivery step be set in a medicament delivery state. This is accomplished by pushing the needle shield 109 towards the distal end of the delivery device, preferably by pushing the proximal end of the needle shield against the patient's skin at the medicament delivery site. When the needle shield moves towards the distal end of the delivery device, the stopper means 111 of the needle shield comes out of engagement with the flanges 130 of the second wheel 128, as seen in FIG. 14, which will not only set the second wheel 128 in a rotatable state but also the first wheel 120, since the wheels 120, 128 are connected via the tubing 124, as described above.

The energy accumulated in the flat spiral spring 114 in the first dose delivery step, will now due to the output torque of the spring 114 when said spring now is free to unwind, rotate the housing member 116 counter clock-wise and also the wheels 120, 128 due to the acting of the protrusions 118 on the teeth 122.

In the plunger-rod-non-rotating-state-configuration, the rotation of the wheels 120, 128 will rotate the plunger rod, and due to non-rotating interior means provided in the interior of the device that hold the plunger rod in a non-rotating state by engaging longitudinal extending means 131 on the rod 126 so that said interior means also is adapted to travel along the longitudinal axis of the rod, the plunger rod 126 is further urged without rotation a predetermined distance towards the proximal end into the cartridge 10. The finer the pitch of grooving, or screw pitch, in the interior of the wheels, i.e. the finer the pitch of grooving of the thread on the rod, the higher the force provided to the piston, when the rod in this case is urged linearly without rotation into the cartridge.

In the plunger-rod-rotating-state-configuration of the second embodiment mentioned above, the rod is urged the predetermined distance towards the proximal end of the cartridge with a rotating movement, with the finer the pitch of grooving of the thread on the rod the higher the force provided to the piston, when the rod in this case is urged with rotation into the cartridge.

Since the proximal end of the plunger rod in any configuration is in contact with the piston sealingly provided inside the cartridge, said piston will move a predetermined distance towards the proximal end of the cartridge and deliver the set volume dose. The device 100 is designed in accordance with the cartridge 103 so that the movement of the piston the predetermined distance towards the proximal end of the cartridge 103, will correspond to the delivery of the dose set in the first dose delivery step corresponding to the set dose.

The housing member and the dose wheel turning member will thus rotate back to its original position when the dose is delivered, whereupon the dose indicating member points out the dose to be delivered. If the cartridge is emptied before the entire dose is delivered, the dose remaining to be taken is pointed out by means of the dose indicating member.

When the dose has been delivered the user releases the needle shield 109, by simply removing the device from the injection site, whereupon the needle shield will move back towards the proximal end of the delivery device by means of the spring force accumulated in the needle shield spring 112 when the needle shield was pressed towards the distal end of the device. The stopper means 111 will now once again engage the flanges 130 of the second wheel 128, which thus sets the delivery device in a non-medicament delivery state, i.e. a non-rotating state of the wheels 120, 128. The plunger rod 126 will stay at its current position, with its proximal end in contact with the piston, and the delivery device 100 is ready to be used again. Preferably the needle is removed and the cap 102 is put back on after use.

The user of the delivery device can also release the needle shield during medicament delivery and hence set the delivery device in the medicament non-delivery state before the set dose has been delivered. The user can then once again push the needle shield towards the distal end of the device, whereby the set dose continues to be delivered. The procedure above can be repeated an optional number of times until the entire set dose has been delivered. This procedure is for instance suitable when a predetermined dose of medicament is to be delivered to a patient at multiple injection sites, whereby the user of the device moves the device from one injection site to another while the delivery device is in the medicament non-delivery state. If the delivery device is used as an inhaler type of device, this procedure is likewise applicable in order to divide the dose of medicament to be inhaled in multiple inhalation steps, as described above in connection with the first embodiment.

If the delivery device 100 needs to be primed before use, this is easily accomplished by setting a small dose volume to be delivered before the first dose delivery step and gently push the needle shield 109 back until a small drop is seen by the end of the needle or a small jet is ejected there from.

If the delivery device 100 is used with a medicament administrating member in the form of a mouth/nasal piece, the function of the needle shield 109 that holds and sets the wheels 120, 128 in a non-rotating and a rotating state, respectively, can be replaced with other suitable means. Such as for instance the dose actuation member 44 described in connection with the first embodiment, that when actuated will release the wheels 120, 128 for rotation. Thus, such a dose actuation member is also provided with stopper means 111 with the above described function. If the device is used as an inhaler device, the means that releases the wheels 120, 128 for rotation can be a breath sensing means, i.e. the wheel are released for rotation by means of the inhalation of the user.

So, with the present invention according to the second embodiment, the force that drives the plunger rod linearly with or without rotation towards the proximal end of the delivery device due to output torque of the flat spiral spring that rotates the plunger rod driving member 128, is in an effective way set to a predetermined force value during the first dose delivery step due to the interacting of the energy accumulating member and the predetermined pitch of grooving, or screw pitch, of the thread on the rod and its interacting components. This set force and the force that acts on the piston is during the entire medicament delivery by design and dimensioning ensured to be above or equal to a minimum force value, which is the lowest force value needed to deliver the set predetermined dose, and is also ensured to be below a maximum force value, which is the first force value at which it exists a risk of damaging the cartridge. FIG. 15 graphically shows the force acting on the piston (F) as a function of the traveled distance (y) by the piston from its original position during medicament delivery, wherein the delivery device first delivers a predetermined dose corresponding to two dose increment steps and thereafter delivers a dose corresponding to four dose increment steps, the indications on the y-axis thus correspond to the dose increment steps. The inclination of the continuous lines, respectively, is identical. As seen, the force is during medicament delivery above and below, respectively, said minimum and maximum force value and the force is thus within a predetermined range. It is to be understood that the force curve obtained with the inventive device according to the second embodiment can have different appearances depending on the type of spring chosen as the energy accumulating member. If for instance a substantially constant force is desired to be applied to the piston, a spiral spring resulting in such a force can easily be provided in the device by the person skilled in the art. The dashed lines 1 and 2 represent the force acting on the piston in a prior art delivery device provided with a helical spring as described by ways of introduction, during the delivery of an amount of medicament corresponding to four dose increment steps. With reference to dashed line 1, the initial force acting on the piston needs to be over the maximum force value in order for the piston to reach the distance in the cartridge that delivers a dose corresponding to four dose increments steps, i.e. there is a risk of damaging the cartridge. If the initial force is lowered, as seen when turning to the dashed line 2, the force acting on the piston will decrease to value below the minimum force value before the piston has reached its required position inside the cartridge and there is a risk that the piston will get stuck before the entire set dose is delivered. Thus, with the present invention, the predetermined dose is ensured to be delivered and the risk for damaging the cartridge or the device due to a too high initial force acting on the piston is substantially reduced, which is a problem with prior art automatic medicament delivery devices.

Moreover, with the present invention according to the second embodiment, there is no longer a need for a pre-tensed helical spring to be provided at high tensioning in the interior of the delivery device in order to provide the plunger rod with a force for driving said rod in the cartridge, in a way that is critical to components that are important for the dose and the dose-to-dose accuracy. Hence, the problem with creep in the plastic materials of the delivery device due to tensions provided by the pre-tensed spring, as discussed above, is effectively and substantially reduced. The problem with plastic deformation is also reduced due to the fact that the force that is applied to the piston does not need to be initially high as with the prior art devices, due to the effective cooperation between the energy accumulating member and the threaded plunger rod of the present invention. That is, having an output torque of a flat spiral spring rotating a plunger rod driving member and having a plunger rod provided with a thread of a predetermined pitch of grooving, or screw pitch, requires less force to act on the piston in comparison with prior art devices. Particularly if friction is reduced by means of for instance low friction washers, lubricant(s), a ball bearing or by using low friction material in the plunger rod and its interacting components.

However, even though the present invention according to the second embodiment has been described and illustrated in detail, said description and said illustrations shall be regarded as being non limited, since it will be appreciated that only the currently preferred embodiment has been shown. The skilled person is for instance fully capable to replace the flat spiral spring with other types of energy accumulating members, such as other types of springs capable of providing an output torque. Moreover, the rotation directions mentioned above, can naturally be the opposite rotation direction by suitable configurations of the device that are readily carried out by the person skilled in the art, so that a counter clock-wise rotation as mentioned above instead is a clock-wise rotation, and vice versa.

The Delivery Device According to a Configuration, Wherein the Dose Steps to be Delivered are Predetermined In a further configuration of the inventive delivery device, preferably applicable to the plunger-rod-rotating-state-configuration of the first embodiment, the delivery device is adapted to deliver predetermined dose steps of the medicament to be delivered, wherein said dose steps is not determined when the dose is about to be delivered but during the manufacturing of the device. This will for instance greatly reduce the risk for overdoses of the medicament. The medicament administrating member is thus in the predetermineddose-step-configuration preferably a needle for the injection of a liquid medicament into the body of the patient. The delivery device of the further configuration will be described below with reference to FIG. 9.

In FIG. 9 is shown the distal part of a delivery device 300. As the device 300 comprises substantially the same components, substantially having the same appearance and substantially cooperating in the same way as described above in connection with the first embodiment and the plunger-rod-rotating-state-configuration thereof, the interacting of said components will not be repeated herein below. The device 300 thus preferably comprises, a dose wheel 4 with a dose wheel turning member 5 and a housing member 6, housing a energy accumulating member in the form of a flat spiral spring 26. The device comprises further a threaded plunger rod 16, a coupling member 34 and a coupling spring 32, said coupling member further comprising a crown 35 with bevelled protrusions 38. As in the plunger-rod-rotating-state-configuration of the first embodiment, the device 300 comprises further a plunger rod driving member 47 provided with a skirt 49 and bevelled recesses 36 as well as a non-rotating bearing 41, provided with an interior tubular formed part 43, even if said part is not shown in FIG. 9, since it is hidden by the plunger rod driving member 47.

However, the exterior of the proximal part of the plunger rod driving member 47 is in the predetermined-dose-step-configuration provided with a number of dose step protrusions 302, equally distributed along the circumference of the proximal part of the member 47. Every other protrusion 302a is however provided a predetermined distance distal to the rest of the protrusions 302b. The protrusions 302a are thus provided equally distributed along the circumference of the member 47 with their centres provided a certain distance from the proximal end of the member 47, and the protrusions 302b are thus also provided equally distributed along the circumference of the member 47 but with their centres provided a shorter distance from the proximal end of the member 47 than the protrusions 302a. The distance between the centres of every protrusion 302 along the circumference of the driving member 47 is however equal if, as in this case, the predetermined dose steps are to be equally large, i.e. every dose step delivers the same predetermined amount of medicament.

The actuation sleeve 304 of the deliver device of the predetermined-dose-step-configuration is provided with an inwardly protruding stopper means 306 adapted to set the plunger rod driving member 47 in a non-rotating state as well as a rotating state. The actuation sleeve 304, and thus also the stopper means 306, is therefore adapted to be moved in the longitudinal direction of the device with a distance that corresponds to the distance between the centres of the protrusions 302a and 302b in the longitudinal direction. That is, when the stopper means 306 abuts against, as seen in FIG. 9, the right hand side of a protrusion 302, the driving member 47 is prevented to be rotated counter-clockwise, i.e. the device 300 is thus in a non-medicament delivery state.

When delivery device 300 is adapted to be used and when said device is in the non-medicament delivery device, i.e. when the plunger rod driving member is in the non-rotating state, the user rotates the dose wheel clock-wise, preferably the maximum number of steps whereby the spiral spring thus winds up an accumulates the largest permitted energy. If the stopper means abut against a protrusion 302a provided closer to the distal end of the member 47 than the protrusions 302b, the user then moves the actuation sleeve 304 and thus also the stopper means 306, the predetermined distance towards the proximal end of the device, whereby the stopper means 306 releases the plunger rod driving member 47 for rotation which sets the device in a medicament delivery state. If the stopper means 306 on the other hand abuts against a protrusion 302b, the user then instead moves the actuation sleeve 304 and thus also the stopper means 306, the predetermined distance towards the distal end of the device, whereby the stopper means 306 releases the plunger rod driving member 47 for rotation.

When the plunger rod driving member 47 is free to rotate, the output torque provided by the spring 26 will, as described above in connection with the plunger-rod-rotating-state-configuration of the first embodiment, rotate the member 47, and hence also the rod 16. However, independent of the energy accumulated in the spring 26, the member 47 will only rotate until the stopper means 306 abuts against the protrusion 302 following the protrusion 302 it previously abutted against in the direction along the circumference of the member 47, whereby the stopper means 306 travels along the circumferential surface of the member 47 the predetermined distance between the two protrusions 302a and 302b in the direction along the circumference of the member 47, each time the member is rotated.

That is, if the stopper means 306 initially abuts against the right hand side of the protrusion referred to as 302a in FIG. 9, the stopper means 306 will after the one step counter clockwise rotation of the member 47, abut against the protrusion referred to as 302b. The next time the user wants to deliver a dose, be then moves the actuation sleeve and the stopper means the predetermined distance towards the distal end of the device, whereby the member 47 rotates another step. This medicament delivery procedure can be repeated until the flat spiral spring has unwound and adapted is original non-energy accumulated state, or until the cartridge is emptied. If the former occurs before the cartridge is emptied, the user may naturally wind up the spiral spring once again. It may be that the manufacturer of the device delivers the device with the spiral spring already in a pre-tensed state, whereby the device should be used as a disposable article, i.e. when the spring has unwound it mat not be used any further.

The amount of medicament corresponding to one dose step, is thus determined by the manufacturer of the device. In the currently preferred design, the rotation of the plunger rod driving member with 30°, will correspond to the travel of the stopper means along the circumferential surface of the member 47 with a distance corresponding to the distance between a protrusion 302a and the following protrusion 302b in the direction along the circumference of the member 47, i.e. the rotation of the plunger rod driving member 47 with 30° corresponds to one dose delivery step. The rotation of the plunger rod driving member 47 with said number of degrees corresponds to the movement of the plunger rod towards the proximal end of the cartridge with a distance of 0.3 mm which in this currently preferred design will deliver 10 µl of medicament.

As mentioned above, the distance between a protrusion 302a and a protrusion 302b in the direction along the circumference of the member 47, will determine the amount of medicament to be delivered. If said distance is equal between every protrusion, the amount of medicament will be identical in every dose step. The manufacturer of the device can, however produce a device comprising a member 47 with protrusions 302, in which the distance between the protrusions in the direction along the circumference of the member is not equal everywhere. Thus, said distance can vary in correspondence with a predetermined pattern giving rise to a predetermined dose step pattern. For instance, the distance between the protrusions in the direction along the circumference of the member can become larger and larger, whereupon the amount of medicament delivered will increase for every dose step until the plunger rod driving member has completed a full turn.

As described above in connection with the first embodiment, the force applied to the piston is also in this predetermined-dose-step-configuration ensured to be with in the predetermined force range due to the cooperation between the energy accumulating member and the predetermined pitch of grooving, i.e. screw pitch, of the thread on the rod. Moreover, even if the predetermined-dose-step-configuration is described with reference to the plunger-rod-rotating-state-configuration of the first embodiment, it is to be understood that the predetermined-dose-step-configuration could be applied to a delivery device according to the first embodiment wherein the plunger rod moves towards the proximal end of the cartridge without rotation, and also with the second embodiment of the delivery device, in theplunger-rod-rotating-state-configuration as well as the plunger-rod-non-rotating-state-configuration.

2. Delivery device
4. Dose Wheel
5. Dose wheel turning member
6. Housing member
7. Splines of dose wheel turning member
8. Cartridge housing
9. Inward protruding means of housing member
10. Cartridge
11. Shoulder
13. Flat spiral spring cover
16. Plunger rod
20. Plunger cap
22. Piston
26. Flat spiral spring
28. Protruding member of flat spiral spring
29. Slit in housing member
30. Bend of flat spiral spring
31. Flat spiral spring holding means
32. Coupling spring
34. Coupling member
35. Crown of coupling member
36. Bevelled recesses of plunger rod driving member
38. Bevelled protrusions of crown
40. Plunger rod driving member
41. Non-rotating bearing
42. Plunger rod driving member flanges
43. Interior part of bearing 41
44. Dose actuation member
45. Sleeve means
46. Axial bearing
47. Plunger rod driving member
48. Outer cover of bearing 46
49. Skirt of nut
50. Actuation sleeve
51. Protruding stopper means of actuation sleeve
52. Interior means of member 47
53. Longitudinal extending means on plunger rod
54. Outer part of bearing 41
55. Outer cover
56. Actuation spring
100. Delivery device
101. Cartridge housing
102. Cap
103. Cartridge
104. Dose wheel turning member
105. Dose indicating member
106. Crown of housing member
107. Slit in outer cover
108. Outer cover
109. Needle shield
111. Needle shield stopper means
112. Needle shield spring
114. Flat spiral spring
116. Housing member
118. Protrusions of crown
120. First wheel
122. Teeth of first wheel
124. Tubing
126. Plunger rod
128. Second wheel
130. Flanges of second wheel
131. Longitudinal extending means on the rod
300. Delivery device
302. Dose step protrusions
304. Actuation sleeve
306. Stopper means of actuation sleeve

The invention claimed is:

1. A device for delivering predetermined doses of liquid medicament, the device having a medicament delivery state and a medicament non-delivery state and comprising:
a cartridge configured to contain the liquid medicament and a piston sealingly and slidably arranged in the cartridge;
an energy accumulating member configured to stepwise accumulate energy when the device is in the medicament non-delivery state;
an elongated threaded plunger rod arranged in an interior of the device;
a plunger rod driving member configured to engage the threaded plunger rod and be in a driven state when the device is in the medicament delivery state and in a non-driven state when the device is in the medicament non-delivery state, wherein rotation of the plunger rod driving member due to output torque of the energy accumulating member drives the threaded plunger rod, enabling the threaded plunger rod, which is in contact with the piston, to be driven toward a proximal end of the cartridge by a predetermined distance and expel a predetermined dose of the liquid medicament from the cartridge; and
an axial bearing coupled to an outer cover and configured to pick up forces acting on a proximal part of the device in a longitudinal direction thereof and arising from driving the threaded plunger rod, whereby more of the accumulated energy that results from stepwise rotational tensioning of the energy accumulating member positioned at a distal end of the device is converted to output torque;
wherein the energy accumulating member is a flat spiral spring.

2. The device of claim 1, further comprising a cartridge housing coupled to the outer cover, wherein an interior part of the cartridge housing engages a longitudinal extending device on the plunger rod, and an interior part of the plunger rod driving member engages the plunger rod with a thread that corresponds to a thread on the plunger rod, so that rotation of the plunger rod driving member drives the plunger rod toward the proximal end of the cartridge by the predetermined distance without rotation.

3. The device of claim 1, wherein an interior part of the plunger rod driving member includes a device that engages a longitudinal extending device on the plunger rod, and an interior part of the bearing includes a thread that corresponds to a thread on the plunger rod, so that the plunger rod moves toward the proximal end of the cartridge by the predetermined distance with rotation.

4. The device of claim 1, further comprising a dose setting member configured to rotate stepwise when the device is in the medicament non-delivery state for stepwise increasing the accumulated energy in the energy accumulating member and to be pulled toward a distal end of the device to release the accumulated energy in the energy accumulating member for cancelling a dose.

5. The device of claim 1, wherein a proximal part of an exterior part of the plunger rod driving member includes outwardly protruding flanges configured to engage an inwardly protruding stopper provided on an interior part of an actuation sleeve when the device is in the medicament non-delivery state.

6. The device of claim 5, wherein the outwardly protruding flanges include a plurality of dose step protrusions equally distributed along a circumference of the proximal part of the plunger rod driving member so that every dose step delivers the same amount of medicament.

7. The device of claim 1, wherein the device during medicament delivery is configured to be set in the medicament non-delivery state before an entire set dose has been delivered, whereupon the plunger rod stops its movement toward the proximal end of the cartridge, and the device thereafter is configured to be set in the medicament delivery state, whereupon the plunger rod continues to move the predetermined distance towards the proximal end of the device.

8. The device of claim 1, wherein the device is configured to be connected to a medicament administering member that is put in a patient's mouth or nose, whereby the predetermined dose of medicament is inhaled by the patient when the delivery device is in the medicament delivery state.

9. The device of claim 1, wherein the device is configured to be connected to a medicament administering member such that the predetermined dose of medicament is sprayed into an eye or onto a skin of a patient when the delivery device is in the medicament delivery state.

10. The device of claim 1, wherein the device is configured to be connected to a medicament administering member that delivers the predetermined dose of medicament as at least one drop when the delivery device is in the medicament delivery state.

11. The device of claim 1, wherein the device is configured to be connected to a medicament administering needle for injecting the predetermined dose of medicament into a body of a patient when the delivery device is in the medicament delivery state.

* * * * *